US007432418B2

(12) United States Patent
Abbitt et al.

(10) Patent No.: US 7,432,418 B2
(45) Date of Patent: Oct. 7, 2008

(54) SEED-PREFERRED REGULATORY ELEMENTS AND USES THEREOF

(75) Inventors: Shane E. Abbitt, Ankeny, IA (US); William J. Gordon-Kamm, Urbandale, IA (US); Keith S. Lowe, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 11/519,184

(22) Filed: Sep. 11, 2006

(65) Prior Publication Data

US 2007/0220626 A1 Sep. 20, 2007

Related U.S. Application Data

(62) Division of application No. 09/718,754, filed on Nov. 22, 2000, now Pat. No. 7,122,658.

(51) Int. Cl.
*C12N 15/29* (2006.01)
*C12N 15/82* (2006.01)
*A01H 5/00* (2006.01)
*A01H 5/10* (2006.01)

(52) U.S. Cl. .................... 800/298; 800/320.1; 800/278; 800/287; 800/290; 536/24.1; 435/320.1

(58) Field of Classification Search ................ 536/24.1; 800/298, 320.1, 278, 287
See application file for complete search history.

(56) References Cited

U.S. PATENT DOCUMENTS 6,037,524 A * 3/2000 Greenland et al. .......... 800/287
6,043,083 A    3/2000 Davis et al.
7,122,658 B1 * 10/2006 Lappegard et al. ......... 536/24.1

FOREIGN PATENT DOCUMENTS

WO    WO 98/37184 A1    8/1998
WO    WO 99/67405 A2   12/1999

OTHER PUBLICATIONS

Kagaya et al (1995, Mol. Gen. Genet. 248 :668-674).*
Benfey et al (1990, Science 250:959-966).*
Benfey et al (1989, EMBO J, 8(8):2195-2202).*
Johnson, M.D., The *Arabidopsis thaliana* myo-Inositol 1-Phosphate Synthase (ED 5.5.1.4), Plant Physiol. (1994) 105: 1023-1024.
Walbot, V., GenBank Accession No. AW066683, Maize ESTs from various cDNA libraries sequenced at Stanford University (1999).
Kurek et al., Isolation and characterization of the wheat prolyl isomerase FK506-binding protein (FKBP) 73 promoter, Plant Mol. Biol. (2000) 42:489-497.
Chen et al., Minimal regions in the *Arabidopsis pistillata* promoter responsive to the Apetala3/Pistillata feedback control do not contain a CArG box, Sex Plant Reprod. (2000) 13:85-94.

Ezcurra et al., Interaction between composite elements in the napA promoter: both the B-box ABA-responsive complex and the RY/G complex are necessary for seed-specific expression, Plant Mol. Biol. (1999) 40:699-709.
Wu et al., Quantitative nature of the Prolamin-box, ACGT and AACA motifs in a rice glutelin gene promoter: minimal cis-element requirements for endosperm-specific gene expression, Plant J. (2000) 23(3):415-421.
Iida et al., Positive and negative cis-regulatory regions in the soybean glycinin promoter identified by quantitative transient gene expression, Plant Cell Reports (1995) 14:539-544.
Lee et al., Jasmonate signalling can be uncoupled from abscisic acid signaling in barley: identification of jasmonate-regulated transcripts which are not induced by abscisic acid, Planta (1996) 625-632.
Lotan et al., *Arabidopsis* Leafy Cotyledon1 Is Sufficient to Induce Embryo Development in Vegetative Cells, Cell (1998) 93:1195-1205.
Smith et al., Temporal and spatial regulation of a novel gene in barley embryos, Plant Molecular Biology (1992) 20:255-266.
Sundaresan et al., Patterns of gene action in plant development revealed by enhancer trap and gene trap transposable elements, Genes & Development (1995) 9:1797-1810.
Walbot, V., 683006D10.x1 683—14 day immature embryo from Hake lab (HS) *Zea mays* cDNA mRNA sequence, Database Accession No. AW066683 (1999).
Lohman et al., A Molecular Link between Stem Cell Regulation and Floral Patterning in *Arabidopsis*, Cell (2001) 105:793-803.
Busch et al., Activation of a Floral Homeotic Gene in *Arabidopsis*, Science (1999) 285:585-587.
Izawa et al., Plant bZIP Protein DNA Binding Specificity, J. Mol. Biol. (1993) 230:1131-1144.
Hao et al., Unique Mode of GCC Box Recognition by the DNA-binding Domain of Ethylene-responsive Element-binding Factor (ERF Domain) in Plant, The Journal of Biological Chemistry (1998) 273(41):26857-26861.
Kagaya et al., The promoter from the rice nuclear gene encoding chloroplast aldolase confers mesophyll-specific and light-regulated expression in transgenic tobacco, Mol. Gen. Genet. (1995) 284:668-674.
Benfey et al., The Cauliflower Mosaic Virus 35S Promoter: Combinatorial Regulation of Transcription in Plants, Science (1990) 250:959-966.
Benfey et al., The CaMV 35S enhancer contains at least two domains which can confer different developmental and tissue-specific expression patterns, EMBO Journal (1989) 8(8):2195-2202.

* cited by examiner

*Primary Examiner*—Stuart F. Baum
(74) *Attorney, Agent, or Firm*—Pioneer Hi-Bred International, Inc.; Kathryn K. Lappegard

(57) ABSTRACT

The present invention provides compositions and methods for regulating expression of isolated nucleotide sequences in a plant. The compositions are novel nucleic acid sequences for callus-tissue and seed embryo-preferred regulatory sequences. Methods for expressing an isolated nucleotide sequence in a plant or callus tissue using the regulatory sequences are also provided. The methods comprise transforming a plant cell to contain an isolated nucleotide sequence operably linked to the regulatory sequences of the present invention and regenerating a stably transformed plant or callus tissue from the transformed plant cell.

12 Claims, No Drawings

SEQUENCE LISTING

```
<160> NUMBER OF SEQ ID NOS: 19

<210> SEQ ID NO 1
<211> LENGTH: 1247
<212> TYPE: DNA
<213> ORGANISM: Zea maize
<220> FEATURE:
<221> NAME/KEY: promoter
<222> LOCATION: (1)...(1247)

<400> SEQUENCE: 1
atcgtacata aagttggatt atacaatatc catttacaac taaatagaaa ccaattaatt      60
taaaaaacta aaaaaacctt tatcaccgta caggagaaga gagcatcaac ttgctattag     120
ttttatgcat ttaaacaccc ttcgaaccat cagcagtggt tgataggttt aactgatact     180
aatatcttgt ctttaatact agcaccaact gataataatc tttcgaacac atgttattat     240
ctattgttga ctttaatcaa tactaaatcc aagatattag tagagatgtt agtatagatt     300
aaggtgatgt ttgaatgcac tagagctaat agttagtagc taaaattagt tggagacatt     360
caaacaccct atcaattatt agttatttt agtaaattag ttaatagtta gttagttatt     420
tataagctag ctttttttac tagcaatttt ttagccaact aacaattagt tttagtgtat     480
tcaaataccc ctaagccgtt aagtgatgct ctttctagaa tcttaaccgt atgtggagac     540
aacattttca taggtgtact gtttaagtca ccgtcagtga taataatatt ttcacatgcg     600
gtttcttaag caaaccgcca gtgctaatga tatttacact agcgggctgc taaagaaaac     660
cgcccgtgct aaagatattt acactagcgg ttggtgaaca actgcctgtg aaaaaagccg     720
attcctacta gcccctagct tgcactggcg acataaaaaa cgtcagtgaa aatagctcta     780
ggatcgtcac tatagagctt ctatgtactt agtggttaga actgatattg tagtgcacca     840
agtgccgatt ttaattaaac caatactaaa tactagtaaa taatactagt ggtctgaatt     900
cgatttctat agtaatgttt gcttgcaagc cgcaaataga gtaaacattc gtcgtcacag     960
aaatccacat tacatcaagg tccatggcgg ccggccacgt acccatccca cgcgtcgctg    1020
cggaggacac gtgttggctg accggacagt tggccgatca gacagtggac agaccggaca    1080
atagaagaag aagacgacga cggcggcggc accgccgagt aggtgcatgg tcacgctagc    1140
tgtagctttt tgcagagcgt cgtctgtaaa tacgtagccc ttccacaagc gaggcaaggg    1200
gggagagagt atcgtcagct agcagagaga gtgcgtagca actagca                 1247

<210> SEQ ID NO 2
```

```
<211> LENGTH: 26
<212> TYPE: DNA
<213> ORGANISM: Artificial Sequence
<220> FEATURE:
<223> OTHER INFORMATION: Jip1 forward primer

<400> SEQUENCE: 2
tcgggagaag tcactagcgg ggaact                                            26

<210> SEQ ID NO 3
<211> LENGTH: 27
<212> TYPE: DNA
<213> ORGANISM: Artificial Sequence
<220> FEATURE:
<221> NAME/KEY: primer_bind
<222> LOCATION: (1)...(27)
<223> OTHER INFORMATION: Jip1 nested forward primer
<220> FEATURE:
<223> OTHER INFORMATION: primer

<400> SEQUENCE: 3
gagcagggtt ctccgccatt gctagtt                                           27

<210> SEQ ID NO 4
<211> LENGTH: 752
<212> TYPE: DNA
<213> ORGANISM: Zea mays
<220> FEATURE:
<221> NAME/KEY: promoter
<222> LOCATION: (1)...(752)

<400> SEQUENCE: 4
aagctttgat caaaagcgcc cgccacttct aaaggtcagg ggtcttgcgt tctgcccctc        60
gtgcttcctt caaattctgg acctagtgga tcaatttacg tacacctcag caaccgatgc       120
agccagtaag tatgatgagc acgattgtga cgtgttgggg tcatggtcaa tggcaaccga       180
gcacgaattg gtagtgtcag cttttttgtac acgtgatagc atttgattcg ttcattcaat      240
ttgaactgtt tgaacttatg tatagagaaa ttagtccaac tcatgtttaa taaatagtat       300
aaaacccatc gaatttctga attatgatag caggtatcca ttgtcatcgc tcagtcacag       360
aggcagccac tgccgacggg cgacggccga cggcctccca tttcgatccc ctcctactcc       420
tatgctgcgg tccagcataa gttcgggact tccggcaatc cgccggcgcc cgtcggctca       480
aatcgcatct accgcggcta aagctctct cttcctccct ccgatccggt ggggtccatt        540
tccttcaatt gtggcagtgg ccgtctcgaa ccctctataa atcccccacc ccggacaccc       600
ttccccgacc acacggtcca cacagcccaa caaaggagcg cggcggcccc tccttccttc       660
ctcccacttc tctcgcgcgg cgctcgctta cctcgcctcg cattccgttc gagcagggga       720
gcggcagtga aagggaggg aattaaggca cc                                      752

<210> SEQ ID NO 5
<211> LENGTH: 30
<212> TYPE: DNA
<213> ORGANISM: Artificial Sequence
<220> FEATURE:
<221> NAME/KEY: primer_bind
<222> LOCATION: (1)...(30)
<223> OTHER INFORMATION: Milps3 forward primer
<220> FEATURE:
<223> OTHER INFORMATION: primer

<400> SEQUENCE: 5
cggaagctct cgatgaacat cttgccttaa                                        30
```

<210> SEQ ID NO 6
<211> LENGTH: 1433
<212> TYPE: DNA
<213> ORGANISM: Zea mays
<220> FEATURE:
<221> NAME/KEY: promoter
<222> LOCATION: (1)...(1433)

<400> SEQUENCE: 6

| | | | | | |
|---|---|---|---|---|---|
| tcctaatctt | caaataacca | tctcaaaagt | tttttaaaac | atcttttgag | gatatgtatc | 60 |
| ccatagccct | agagcgctaa | attgactact | tttagtcgat | taaaaggtat | tagacatcct | 120 |
| tacaagtcct | aagtatcaaa | tcaccttcta | tcggctatac | acaactaacg | gaagttatct | 180 |
| ctagtcacac | taacttatgt | cggtttccgc | atggcagatc | aaaattagct | aacttttgtt | 240 |
| ggctaataag | agcaattcca | aaagaacgtg | taaactaatc | tcaaaacaga | tattagttaa | 300 |
| gaatagtaat | ttttcttact | ccaacagttc | cctcagtctt | ccccaaaaaa | ttaagcgttc | 360 |
| cgcatccaca | gcctcctctc | ggtcgtattt | tggtgtgttt | catccctccc | caatccattt | 420 |
| ctcaacgtat | cagatcatcc | accgcctacg | acgactgtac | agtttgcgtc | acatatcaca | 480 |
| tttaaaggaa | ctgttggagt | acccatcata | attcactctt | aaaaaatttt | agcctgctct | 540 |
| caataatcaa | ttgggggggt | aaaatttta | acatccttc | ggatctaatc | caacttatgg | 600 |
| aagttagcta | gctctggtcg | cgctaacttc | tgtcgatcgc | ctattagcta | atactccatc | 660 |
| tgtcccatta | tataaggtat | aaccaactct | gattcaaaga | ccaaaaatat | acttaattgt | 720 |
| gtctatacca | cttcatcgat | gtacgtatgc | atagaaagag | cacatcttat | attgtggaac | 780 |
| aagaacaaaa | atatggttac | gccttatatt | ataagacgta | gaaatcaatg | gtttacaata | 840 |
| gccaagaata | gatgttttta | tttatttcct | atatagatgt | tttttatttat | ttcctatatg | 900 |
| tttcacaata | gccttatatt | gtgccgaaaa | tttaggcaca | cgtgccacga | acgtctgaaa | 960 |
| tgtactccgc | gcgtattacc | atgcactacg | acgtacgtag | gagtatgtac | gttgaaccaa | 1020 |
| gcacacatat | atctctgaca | cagtacaatg | atatactaca | acaacaacag | tactgcccaa | 1080 |
| ttcatccatt | ttcacgttcc | atcttccgcg | tgtgacaact | cgatcggcca | cgcacgcaga | 1140 |
| cgacgacgga | gcagtacttc | acagaatcct | ccgccactcg | tcacaccaac | aggcgcgcgc | 1200 |
| tggtgcgcat | gcatcatgtg | catgccatcg | tccgtccctt | ggcgtgcctc | ggtagacggt | 1260 |
| agctagagta | gtagcctgtg | cttgctaccc | ctggtcaaca | catcgtagcc | tcctatattt | 1320 |
| aacgtatcct | cacacatcac | aagaacgaca | cacagaaacc | agtagccact | actccatcca | 1380 |
| ccacgagcga | gcgagcgata | accctagcta | gcttcaggat | ccagcgagag | ccc | 1433 |

<210> SEQ ID NO 7
<211> LENGTH: 20
<212> TYPE: DNA
<213> ORGANISM: Artificial Sequence
<220> FEATURE:
<221> NAME/KEY: primer_bind
<222> LOCATION: (1)...(20)
<223> OTHER INFORMATION: Lec 1 prom. forward probe
<220> FEATURE:
<223> OTHER INFORMATION: primer

<400> SEQUENCE: 7
acaccacgag cgcgcgataa                                                20

<210> SEQ ID NO 8
<211> LENGTH: 20

```
<212> TYPE: DNA
<213> ORGANISM: Artificial Sequence
<220> FEATURE:
<221> NAME/KEY: primer_bind
<222> LOCATION: (1)...(20)
<223> OTHER INFORMATION: Lec 1 prom. reverse probe
<220> FEATURE:
<223> OTHER INFORMATION: primer

<400> SEQUENCE: 8
tggtggtggt gcggtagcat                                              20

<210> SEQ ID NO 9
<211> LENGTH: 695
<212> TYPE: DNA
<213> ORGANISM: Zea mays
<220> FEATURE:
<221> NAME/KEY: terminator
<222> LOCATION: (1)...(695)

<400> SEQUENCE: 9
tacctagttc gtacgtcgtt cgacttgagc aagccatcga tctgctgatc tgaacgtacg    60
ctgtattgta cacgcatgca cgtacgtatc ggcggctagc tctcctgttt aagttgtact   120
gtgattctgt cccggccggc tagcaactta gtatcttcct tcagtctcta gtttcttagc   180
agtcgtagaa gtgttcaatg cttgccagtg tgttgtttta gggccggggt aaaccatccg   240
atgagattat ttcatgcacg cttttagac tgacgactgt tcgtgtgtgt cttctgcgca    300
gttccgctcc tagcacaatt atatcatcct tgatgatcgt ttaacgcaac agtcttctct   360
ggaggtctag acctagcgga tcttttgttg tactcccttc tatacgtaca tgcatactac   420
acgtacgtac ggcggcggta cggcagctac atattcgtcg ttcgagtgtg atgcatgggt   480 tgtcttttaaa gcccttcgtc gttctagctg ctggcctgct gctatagcct gtaggtgagg   540
tgttcgtggc ttgcgacgcg cgggaggaag cacgacggac ggtggcggcg catgttcttg   600
actctggact attgcgcgta ggcgcgtgac caagttccac ggtggcgtgc gcggctgcag   660
cgaggcgccc gcgacaagtg ccggcgatcc cgcag                             695

<210> SEQ ID NO 10
<211> LENGTH: 45
<212> TYPE: DNA
<213> ORGANISM: Artificial Sequence
<220> FEATURE:
<221> NAME/KEY: primer_bind
<222> LOCATION: (1)...(45)
<223> OTHER INFORMATION: Lec1 term. forward primer
<220> FEATURE:
<223> OTHER INFORMATION: primer

<400> SEQUENCE: 10
gtcgacagat ctgttaacct agttcgtacg tcgttcgact tgagc                   45

<210> SEQ ID NO 11
<211> LENGTH: 36
<212> TYPE: DNA
<213> ORGANISM: Artificial Sequence
<220> FEATURE:
<221> NAME/KEY: primer_bind
<222> LOCATION: (1)...(36)
<223> OTHER INFORMATION: Lec1 term. reverse primer
<220> FEATURE:
<223> OTHER INFORMATION: primer

<400> SEQUENCE: 11 gggcccgtg cggcaacaaa aatagacctg acctca                              36
```

<210> SEQ ID NO 12
<211> LENGTH: 29
<212> TYPE: DNA
<213> ORGANISM: Artificial Sequence
<220> FEATURE:
<221> NAME/KEY: primer_bind
<222> LOCATION: (1)...(29)
<223> OTHER INFORMATION: Jip1 forward nested primer
<220> FEATURE:
<223> OTHER INFORMATION: primer

<400> SEQUENCE: 12
cctttatcac cgtacaggag aagagagca                          29

<210> SEQ ID NO 13
<211> LENGTH: 26
<212> TYPE: DNA
<213> ORGANISM: Artificial Sequence
<220> FEATURE:
<221> NAME/KEY: primer_bind
<222> LOCATION: (1)...(26)
<223> OTHER INFORMATION: Jip1 reverse nested primer
<220> FEATURE:
<223> OTHER INFORMATION: primer

<400> SEQUENCE: 13
tattgtccgg tctgtccact gtctga                             26

<210> SEQ ID NO 14
<211> LENGTH: 28
<212> TYPE: DNA
<213> ORGANISM: Artificial Sequence
<220> FEATURE:
<221> NAME/KEY: primer_bind
<222> LOCATION: (1)...(28)
<223> OTHER INFORMATION: Mi1ps3 nested forward primer
<220> FEATURE:
<223> OTHER INFORMATION: primer

<400> SEQUENCE: 14
gagctcctcc acgcgatcaa aagcgccc                           28

<210> SEQ ID NO 15
<211> LENGTH: 37
<212> TYPE: DNA
<213> ORGANISM: Artificial Sequence
<220> FEATURE:
<221> NAME/KEY: primer_bind
<222> LOCATION: (1)...(37)
<223> OTHER INFORMATION: Mi1ps3 nested reverse primer
<220> FEATURE:
<223> OTHER INFORMATION: primer

<400> SEQUENCE: 15
cccgggccat ggtcatgcct taattccctc ccttctc                 37

<210> SEQ ID NO 16
<211> LENGTH: 29
<212> TYPE: DNA
<213> ORGANISM: Artificial Sequence
<220> FEATURE:
<221> NAME/KEY: primer_bind
<222> LOCATION: (1)...(29)
<223> OTHER INFORMATION: Lec1 promoter forward nested primer
<220> FEATURE:

-continued

```
<223> OTHER INFORMATION: primer

<400> SEQUENCE: 16
tcgaggtcga cggtatcgat aagcttcct                                              29

<210> SEQ ID NO 17
<211> LENGTH: 49
<212> TYPE: DNA
<213> ORGANISM: Artificial Sequence
<220> FEATURE:
<221> NAME/KEY: primer_bind
<222> LOCATION: (1)...(49)
<223> OTHER INFORMATION: Lec1 nested reverse primer
<220> FEATURE:
<223> OTHER INFORMATION: primer

<400> SEQUENCE: 17
gtcgacccat gggctctcgc tggatcctga agctagctag ggttatcgc                        49

<210> SEQ ID NO 18
<211> LENGTH: 45
<212> TYPE: DNA
<213> ORGANISM: Artificial Sequence
<220> FEATURE:
<221> NAME/KEY: primer_bind
<222> LOCATION: (1)...(45)
<223> OTHER INFORMATION: Lec1 term. forward nested primer
<220> FEATURE:
<223> OTHER INFORMATION: primer

<400> SEQUENCE: 18
gtcgacagat ctgttaacct agttcgtacg tcgttcgact tgagc                            45

<210> SEQ ID NO 19
<211> LENGTH: 36
<212> TYPE: DNA
<213> ORGANISM: Artificial Sequence
<220> FEATURE:
<221> NAME/KEY: primer_bind
<222> LOCATION: (1)...(36)
<223> OTHER INFORMATION: Lec1 term. reverse nested primer
<220> FEATURE:
<223> OTHER INFORMATION: primer

<400> SEQUENCE: 19
gggccccgtg cggcaacaaa aatagacctg acctca                                      36
```

SEED-PREFERRED REGULATORY ELEMENTS AND USES THEREOF

CROSS REFERENCE TO RELATED APPLICATIONS

This application is a divisional of application Ser. No. 09/718,754 filed Nov. 22, 2000 now U.S. Pat. No. 7,122,658 issued Oct. 17, 2006, the disclosure of which is herein incorporated by reference.

FIELD OF THE INVENTION

The present invention relates to the field of plant molecular biology, more particularly to regulation of gene expression in plants.

BACKGROUND OF THE INVENTION

Expression of isolated DNA sequences in a plant host is dependent upon the presence of operably linked regulatory elements that are functional within the plant host. Choice of the regulatory sequences will determine when and where within the organism the isolated DNA sequence is expressed. Where continuous expression is desired throughout the cells of a plant, constitutive promoters are utilized. In contrast, where gene expression in response to a stimulus is desired, inducible promoters are the regulatory element of choice. Where expression in specific tissues or organs are desired, tissue-preferred promoters and/or terminators are used. That is, these regulatory elements can drive expression in specific tissues or organs. Additional regulatory sequences upstream and/or downstream from the core sequences can be included in expression cassettes of transformation vectors to bring about varying levels of expression of isolated nucleotide sequences in a transgenic plant.

Seed development involves embryogenesis and maturation events as well as physiological adaptation processes that occur within the seed to insure progeny survival. Developing plant seeds accumulate and store carbohydrate, lipid, and protein that are subsequently used during germination. Expression of storage protein genes in seeds occurs primarily in the embryonic axis and cotyledons and in the endosperm of developing seeds but never in mature vegetative tissues. Generally, the expression patterns of seed proteins are highly regulated. This regulation includes spatial and temporal regulation during seed development. A variety of proteins accumulate and decay during embryogenesis and seed development and provide an excellent system for investigating different aspects of gene regulation as well as for providing regulatory sequences for use in genetic manipulation of plants.

Isolation and characterization of seed-preferred promoters and terminators that can serve as regulatory elements for expression of isolated nucleotide sequences of interest in a seed-preferred manner are needed for improving seed traits in plants.

DETAILED DESCRIPTION OF THE INVENTION

In accordance with the invention, nucleotide sequences are provided that allow initiation of transcription in seed. The sequences of the invention comprise transcriptional initiation regions associated with seed formation and seed tissues. Thus, the compositions of the present invention comprise novel nucleotide sequences for plant regulatory elements natively associated with the nucleotide sequences coding for maize Jip1 (jasmonate-induced protein), maize mi1ps3, (myo-inositol 1 phosphate synthase 3) and maize Lec1 (leafy cotyledon 1).

A method for expressing an isolated nucleotide sequence in a plant using the transcriptional initiation sequences disclosed herein is provided. The method comprises transforming a plant cell with a transformation vector that comprises an isolated nucleotide sequence operably linked to one or more of the plant regulatory sequences of the present invention and regenerating a stably transformed plant from the transformed plant cell. In this manner, the regulatory sequences are useful for controlling the expression of endogenous as well as exogenous products in a seed-preferred manner.

Under the transcriptional initiation regulation of the seed-specific region will be a sequence of interest, which will provide for modification of the phenotype of the seed. Such modification includes modulating the production of an endogenous product, as to amount, relative distribution, or the like, or production of an exogenous expression product to provide for a novel function or product in the seed.

By "seed-preferred" is intended favored expression in the seed, including at least one of embryo, kernel, pericarp, endosperm, nucellus, aleurone, pedicel, and the like.

By "regulatory element" is intended sequences responsible for tissue and temporal expression of the associated coding sequence including promoters, terminators, enhancers, introns, and the like.

By "terminator" is intended sequences that are needed for termination of transcription. A regulatory region of DNA that causes RNA polymerase to disassociate from DNA, causing termination of transcription.

By "promoter" is intended a regulatory region of DNA usually comprising a TATA box capable of directing RNA polymerase II to initiate RNA synthesis at the appropriate transcription initiation site for a particular coding sequence. A promoter can additionally comprise other recognition sequences generally positioned upstream or 5' to the TATA box, referred to as upstream promoter elements, which influence the transcription initiation rate. It is recognized that having identified the nucleotide sequences for the promoter region disclosed herein, it is within the state of the art to isolate and identify further regulatory elements in the 5' untranslated region upstream from the particular promoter region identified herein. Thus the promoter region disclosed herein is generally further defined by comprising upstream regulatory elements such as those responsible for tissue and temporal expression of the coding sequence, enhancers and the like. In the same manner, the promoter elements which enable expression in the desired tissue such as the seed can be identified, isolated, and used with other core promoters to confirm seed-preferred expression.

The isolated promoter sequences of the present invention can be modified to provide for a range of expression levels of the isolated nucleotide sequence. Less than the entire promoter region can be utilized and the ability to drive seed-preferred expression retained. However, it is recognized that expression levels of mRNA can be decreased with deletions of portions of the promoter sequence. Thus, the promoter can be modified to be a weak or strong promoter. Generally, by "weak promoter" is intended a promoter that drives expression of a coding sequence at a low level. By "low level" is intended levels of about $1/10,000$ transcripts to about $1/100,000$ transcripts to about $1/500,000$ transcripts. Conversely, a strong promoter drives expression of a coding sequence at a high level, or at about $1/10$ transcripts to about $1/100$ transcripts to about $1/1,000$ transcripts. Generally, at least about 20 nucleotides of an isolated promoter sequence will be used to drive expression of a nucleotide sequence.

It is recognized that to increase transcription levels enhancers can be utilized in combination with the promoter regions of the invention. Enhancers are nucleotide sequences that act to increase the expression of a promoter region. Enhancers are known in the art and include the SV40 enhancer region, the 35S enhancer element, and the like.

The promoters of the present invention can be isolated from the 5' untranslated region flanking its respective transcription initiation site. Likewise the terminator can be isolated from the 3' untranslated region flanking its respective stop codon. The term "isolated" refers to material, such as a nucleic acid or protein, which is: (1) substantially or essentially free from components which normally accompany or interact with the material as found in its naturally occurring environment or (2) if the material is in its natural environment, the material has been altered by deliberate human intervention to a composition and/or placed at a locus in a cell other than the locus native to the material. Methods for isolation of promoter regions are well known in the art. One method is described in U.S. patent application Ser. No. 06/098,690 filed Aug. 31,1998 herein incorporated by reference. The sequences for the promoter regions are set forth in SEQ ID NOS: 1, 4, and 6.

The Jip1 promoter set forth in SEQ ID NO: 1 is 1,241 nucleotides in length. A putative CAAT motif is found from position 861-864 and a putative TATA motif is found from position 881-885. The promoter was isolated from a coding sequence found in maize tissue libraries of 11 to 30 DAP (days after pollination) endosperm and 13 to 40 DAP embryo. The coding region has 40% homology to a barley jasmonate-induced protein. The promoter can be isolated with the primers of SEQ ID NOS: 2 and 3. The Jip1 promoter can address expression problems by providing expression throughout the whole seed over a broad window of development.

The mi1ps3 promoter set forth in SEQ ID NO: 4 is 752 nucleotides in length. A putative CAAT motif is found from position 546-549 and a putative TATA motif is found from position 576-580. The promoter was isolated from a coding sequence found in maize tissue libraries of 13 to 40 DAP embryo. The coding region has 94% homology to maize mi1ps. The promoter can be isolated with the primers of SEQ ID NOS: 5 and 6. The mi1ps3 promoter can address expression problems by directing expression preferentially to the embryo from mid-to-late development.

The Lec1 promoter set forth in SEQ ID NO: 6 is 1,433 nucleotides in length. A putative CAAT motif is found from position 836-839 and a putative TATA motif is found from position 870-873. The promoter was isolated from a coding sequence found in maize tissue libraries of 13 to 20 DAP (days after pollination) embryo and callus tissue. The coding region was identified according to the procedure described in WO 00/28058 filed Nov. 9,1998, incorporated herein by reference. The promoter can be isolated with the primers/probes of SEQ ID NOS: 7 and 8. The Lec1 promoter can provide expression during early embryo development and during the callus stage of plant regeneration.

The promoter regions of the invention may be isolated from any plant, including, but not limited to corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats, barley, vegetables, ornamentals, and conifers. Preferably, plants include corn, soybean, sunflower, safflower, canola, wheat, barley, rye, alfalfa, and sorghum.

Promoter sequences from other plants may be isolated according to well-known techniques based on their sequence homology to the promoter sequences set forth herein. In these techniques, all or part of the known promoter sequence is used as a probe which selectively hybridizes to other sequences present in a population of cloned genomic DNA fragments (i.e. genomic libraries) from a chosen organism. Methods are readily available in the art for the hybridization of nucleic acid sequences.

The entire promoter sequence or portions thereof can be used as a probe capable of specifically hybridizing to corresponding promoter sequences. To achieve specific hybridization under a variety of conditions, such probes include sequences that are unique and are preferably at least about 10 nucleotides in length, and most preferably at least about 20 nucleotides in length. Such probes can be used to amplify corresponding promoter sequences from a chosen organism by the well-known process of polymerase chain reaction (PCR). This technique can be used to isolate additional promoter sequences from a desired organism or as a diagnostic assay to determine the presence of the promoter sequence in an organism. Examples include hybridization screening of plated DNA libraries (either plaques or colonies; see e.g. Innis et al. (1990) *PCR Protocols, A Guide to Methods and Applications*, eds., Academic Press).

The terms "stringent conditions" or "stringent hybridization conditions" includes reference to conditions under which a probe will hybridize to its target sequence, to a detectably greater degree than other sequences (e.g., at least 2-fold over background). Stringent conditions are target-sequence dependent and will differ depending on the structure of the polynucleotide. By controlling the stringency of the hybridization and/or washing conditions, target sequences can be identified which are 100% complementary to a probe (homologous probing). Alternatively, stringency conditions can be adjusted to allow some mismatching in sequences so that lower degrees of similarity are detected (heterologous probing). Generally, probes of this type are in a range of about 250 nucleotides in length to about 1000 nucleotides in length.

An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-lnterscience, New York (1995). See also Sambrook et al. (1989) *Molecular Cloning: A Laboratory Manual* (2nd ed. Cold Spring Harbor Laboratory, Cold Spring Harbor, N.Y.).

In general, sequences that correspond to the promoter sequence of the present invention and hybridize to the promoter sequence disclosed herein will be at least 50% homologous, 55% homologous, 60% homologous, 65% homologous, 70% homologous, 75% homologous, 80% homologous, 85% homologous, 90% homologous, 95% homologous and even 98% homologous or more with the disclosed sequence.

Specificity is typically the function of post-hybridization washes, the critical factors being the ionic strength and temperature of the final wash solution. Generally, stringent wash temperature conditions are selected to be about 5° C. to about 2° C. lower than the melting point ($T_m$) for the specific sequence at a defined ionic strength and pH. The melting point, or denaturation, of DNA occurs over a narrow temperature range and represents the disruption of the double helix into its complementary single strands. The process is described by the temperature of the midpoint of transition, $T_m$, which is also called the melting temperature. Formulas are available in the art for the determination of melting temperatures.

Hybridization conditions for the promoter sequences of the invention include hybridization at 42° C. in 50% (w/v) formamide, 6×SSC, 0.5% (w/v) SDS, 100 µg/ml salmon sperm DNA. Exemplary low stringency washing conditions include hybridization at 42° C. in a solution of 2×SSC, 0.5% (w/v) SDS for 30 minutes and repeating. Exemplary moderate stringency conditions include a wash in 2×SSC, 0.5% (w/v) SDS at 50° C. for 30 minutes and repeating. Exemplary high stringency conditions include a wash in 2×SSC, 0.5% (w/v) SDS, at 65° C. for 30 minutes and repeating. Sequences that correspond to the promoter of the present invention may be obtained using all the above conditions.

The following terms are used to describe the sequence relationships between two or more nucleic acids or polynucleotides: (a) "reference sequence", (b) "comparison window", (c) "percentage of sequence identity", and (d) "substantial identity".

(a) As used herein, "reference sequence" is a defined sequence used as a basis for sequence comparison. A reference sequence may be a subset or the entirety of a specified sequence; for example, as a segment of a full-length promoter sequence, or the complete promoter sequence.

(b) As used herein, "comparison window" makes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length and optionally can be 30, 40, 50, 100, or more contiguous nucleotides in length. Those of skill in the art understand that to avoid a high similarity to a reference sequence due to inclusion of gaps in the polynucleotide sequence a gap penalty is typically introduced and is subtracted from the number of matches.

(c) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

(d) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters.

Methods of aligning sequences for comparison are well known in the art. Gene comparisons can be determined by conducting BLAST (Basic Local Alignment Search Tool; Altschul, S. F., et al., (1993) *J. Mol. Biol.* 215:403-410; see also www.ncbi.nlm.nih.gov/BLAST/) searches under default parameters for identity to sequences contained in the BLAST "GENEMBL" database. A sequence can be analyzed for identity to all publicly available DNA sequences contained in the GENEMBL database using the BLASTN algorithm under the default parameters. Identity to the sequence of the present invention would mean a polynucleotide sequence having at least 65% sequence identity, more preferably at least 70% sequence identity, more preferably at least 75% sequence identity, more preferably at least 80% identity, more preferably at least 85% sequence identity, more preferably at least 90% sequence identity and most preferably at least 95% sequence identity wherein the percent sequence identity is based on the entire promoter region.

GAP uses the algorithm of Needleman and Wunsch (J. Mol. Biol. 48:443-453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) Proc. Natl. Acad. Sci. USA 89:10915).

Sequence fragments with high percent identity to the sequences of the present invention also refer to those fragments of a particular regulatory element nucleotide sequence disclosed herein that operate to promote the seed-preferred expression of an operably linked isolated nucleotide sequence. These fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequence disclosed herein. The nucleotides of such fragments will usually comprise the TATA recognition sequence of the particular promoter sequence. Such fragments can be obtained by use of restriction enzymes to cleave the naturally occurring regulatory element nucleotide sequences disclosed herein; by synthesizing a nucleotide sequence from the naturally occurring DNA sequence; or can be obtained through the use of PCR technology. See particularly, Mullis et al. (1987) *Methods Enzymol.* 155:335-350, and Erlich, ed. (1989) *PCR Technology* (Stockton Press, New York). Again, variants of these fragments, such as those resulting from site-directed mutagenesis, are encompassed by the compositions of the present invention.

Nucleotide sequences comprising at least about 20 contiguous sequences of the sequence set forth in SEQ ID NOS: 1, 4, 6, are encompassed. These sequences can be isolated by hybridization, PCR, and the like. Such sequences encompass fragments capable of driving seed-preferred expression, fragments useful as probes to identify similar sequences, as well as elements responsible for temporal or tissue specificity.

Biologically active variants of the regulatory sequences are also encompassed by the compositions of the present invention. A regulatory "variant" is a modified form of a regulatory sequence wherein one or more bases have been modified, removed or added. For example, a routine way to remove part of a DNA sequence is to use an exonuclease in combination with DNA amplification to produce unidirectional nested deletions of double stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at 5' overhangs, blunt ends or nicks in the DNA template. However, exonuclease III is unable to remove nucleotides at 3', 4-base overhangs. Timed digests of a clone with this enzyme produces unidirectional nested deletions.

One example of a regulatory sequence variant is a promoter formed by one or more deletions from a larger promoter. The 5' portion of a promoter up to the TATA box near the transcription start site can be deleted without abolishing promoter activity, as described by Zhu et al., *The Plant Cell* 7: 1681-89 (1995). Such variants should retain promoter activity, particularly the ability to drive expression in seed or seed tissues. Biologically active variants include, for example, the native regulatory sequences of the invention having one or more nucleotide substitutions, deletions or insertions. Activity can be measured by Northern blot analysis, reporter activity measurements when using transcriptional fusions, and the like. See, for example, Sambrook et al. (1989) *Molecular Cloning: A Laboratory Manual* (2nd ed. Cold Spring Harbor Laboratory, Cold Spring Harbor, N.Y.), herein incorporated by reference.

The nucleotide sequences for the seed-preferred regulatory elements disclosed in the present invention, as well as variants and fragments thereof, are useful in the genetic manipulation of any plant when operably linked with an isolated nucleotide sequence whose expression is to be controlled to achieve a desired phenotypic response. By "operably linked" is intended the transcription or translation of the isolated nucleotide sequence is under the influence of the regulatory sequence. In this manner, the nucleotide sequences for the regulatory elements of the invention may be provided in expression cassettes along with isolated nucleotide sequences for expression in the plant of interest, more particularly in the seed of the plant. Such an expression cassette is provided with a plurality of restriction sites for insertion of the nucleotide sequence to be under the transcriptional control of the regulatory elements.

The genes of interest expressed by the regulatory elements of the invention can be used for varying the phenotype of seeds. This can be achieved by increasing expression of endogenous or exogenous products in seeds. Alternatively, the results can be achieved by providing for a reduction of expression of one or more endogenous products, particularly enzymes or cofactors in the seed. These modifications result in a change in phenotype of the transformed seed. It is recognized that the regulatory elements may be used with their native coding sequences to increase or decrease expression resulting in a change in phenotype in the transformed seed.

In another embodiment, the regulatory elements of the invention can be used for callus-preferred expression of selectable markers. For example, regulatory elements such as the Lec1 promoter and terminator would allow plants to be regenerated that have no field resistance to herbicide but may be completely susceptible to the herbicide in the callus stage.

General categories of genes of interest for the purposes of the present invention include for example, those genes involved in information, such as Zinc fingers; those involved in communication, such as kinases; and those involved in housekeeping, such as heat shock proteins. More specific categories of transgenes include genes encoding important traits for agronomics, insect resistance, disease resistance, herbicide resistance, and grain characteristics. Still other categories of transgenes include genes for inducing expression of exogenous products such as enzymes, cofactors, and hormones from plants and other eukaryotes as well as prokaryotic organisms. It is recognized that any gene of interest, including the native coding sequence, can be operably linked to the regulatory elements of the invention and expressed in the seed.

Modifications that affect grain traits include increasing the content of oleic acid, or altering levels of saturated and unsaturated fatty acids. Likewise, increasing the levels of lysine and sulfur-containing amino acids may be desired as well as the modification of starch type and content in the seed. Hordothionin protein modifications are described in WO 9416078 filed Apr. 10, 1997; WO 9638562 filed Mar. 26, 1997; WO 9638563 filed Mar. 26, 1997 and U.S. Pat. No. 5,703,409 issued Dec. 30, 1997; the disclosures of which are incorporated herein by reference. Another example is lysine and/or sulfur-rich seed protein encoded by the soybean 2S albumin described in WO 9735023 filed Mar. 20, 1996, and the chymotrypsin inhibitor from barley, Williamson et al. (1987) *Eur. J Biochem.* 165:99-106, the disclosures of each are incorporated by reference.

Derivatives of the following genes can be made by site-directed mutagenesis to increase the level of preselected amino acids in the encoded polypeptide. For example, the gene encoding the barley high lysine polypeptide (BHL), is derived from barley chymotrypsin inhibitor, WO 9820133 filed Nov. 1, 1996 the disclosure of which is incorporated herein by reference. Other proteins include methionine-rich plant proteins such as from sunflower seed, Lilley et al. (1989) *Proceedings of the World Congress on Vegetable Protein Utilization in Human Foods and Animal Feedstuffs*; Applewhite, H. (ed.); American Oil Chemists Soc., Champaign, Ill. :497-502, incorporated herein by reference; corn, Pedersen et al. (1986) *J. Biol. Chem.* 261:6279; Kirihara et al. (1988) *Gene* 71:359, both incorporated herein by reference; and rice, Musumura et al. (1989) *Plant Mol. Biol.* 12:123, incorporated herein by reference. Other important genes encode glucans, Floury 2, growth factors, seed storage factors and transcription factors.

Agronomic traits in seeds can be improved by altering expression of genes that: affect the response of seed growth and development during environmental stress, Cheikh-N et al (1994) *Plant Physiol.* 106(1):45-51) and genes controlling carbohydrate metabolism to reduce kernel abortion in maize, Zinselmeier et al. (1995) *Plant Physiol.* 107(2):385-391.

Insect resistance genes may encode resistance to pests that have great yield drag such as rootworm, cutworm, European Corn Borer, and the like. Such genes include, for example: *Bacillus thuringiensis* endotoxin genes, U.S. Pat. Nos. 5,366,892; 5,747,450; 5,737,514; 5,723,756; 5,593,881; Geiser et al. (1986) *Gene* 48:109; lectins, Van Damme et al. (1994) *Plant Mol. Biol.* 24:825; and the like.

Genes encoding disease resistance traits include: detoxification genes, such as against fumonosin (WO 9606175 filed Jun. 7, 1995); avirulence (avr) and disease resistance (R) genes, Jones et al. (1994) *Science* 266:789; Martin et al. (1993) *Science* 262:1432; Mindrinos et al. (1994) *Cell* 78:1089; and the like.

Commercial traits can also be encoded on a gene(s) which could alter or increase for example, starch for the production of paper, textiles and ethanol, or provide expression of proteins with other commercial uses. Another important commercial use of transformed plants is the production of polymers and bioplastics such as described in U.S. Pat. No. 5,602,321 issued Feb. 11, 1997. Genes such as B-Ketothiolase, PHBase (polyhydroxyburyrate synthase) and acetoacetyl-CoA reductase (see Schubert et al. (1988) *J. Bacteriol* 170 (12):5837-5847) facilitate expression of polyhyroxyalkanoates (PHAs).

Exogenous products include plant enzymes and products as well as those from other sources including prokaryotes and other eukaryotes. Such products include enzymes, cofactors, hormones, and the like. The level of seed proteins, particularly modified seed proteins having improved amino acid distribution to improve the nutrient value of the seed can be increased. This is achieved by the expression of such proteins having enhanced amino acid content.

The nucleotide sequence operably linked to the regulatory elements disclosed herein can be an antisense sequence for a targeted gene. By "antisense DNA nucleotide sequence" is intended a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing with the endogenous messenger RNA (mRNA) produced by transcription of the DNA nucleotide sequence for the targeted gene. In this case, production of the native protein encoded by the targeted gene is inhibited to achieve a desired phenotypic response. Thus the regulatory sequences disclosed herein can be operably linked to antisense DNA sequences to reduce or inhibit expression of a native protein in the plant seed.

The expression cassette will also include at the 3' terminus of the isolated nucleotide sequence of interest, a transcriptional and translational termination region functional in plants. The termination region can be native with the promoter nucleotide sequence of the present invention, can be native with the DNA sequence of interest, or can be derived from another source.

The Lec1 terminator set forth in SEQ ID NO: 10 is 695 nucleotides in length. The terminator was isolated from a coding sequence found in maize tissue libraries of 13 to 20 DAP (days after pollination) embryo and callus tissue. The coding region was identified according to the procedure described in WO 00/28058 filed Nov. 9, 1998, incorporated herein by reference. The terminator can be isolated with the primers/probes of SEQ ID NOS: 11 and 12. The Lec1 terminator, with the appropriate promoter, can provide expression during early embryo development and during the callus stage of plant regeneration. The Lec1 terminator can be used with the Lec1 promoter in an expression cassette, or can be used with another appropriate promoter to provide seed-preferred or callus-preferred expression of a coding region.

Other convenient termination regions are available from the Ti-plasmid of *A. tumefaciens*, such as the octopine synthase and nopaline synthase termination regions. See also: Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. 1989) *Nucleic Acids Res.* 17:7891-7903; Joshi et al. (1987) *Nucleic Acid Res.* 15:9627-9639.

The expression cassettes can additionally contain 5' leader sequences. Such leader sequences can act to enhance translation. Translation leaders are known in the art and include: picornavirus leaders, for example: EMCV leader (Encephalomyocarditis 5' noncoding region), Elroy-Stein et al. (1989) *Proc. Nat. Acad. Sci.* USA 86:6126-6130; potyvirus leaders, for example, TEV leader (Tobacco Etch Virus), Allison et al. (1986); MDMV leader (Maize Dwarf Mosaic Virus), *Virology* 154:9-20; human immunoglobulin heavy-chain binding protein (BiP), Macejak et al. (1991) *Nature* 353:90-94; untranslated leader from the coat protein mRNA of alfalfa mosaic virus (AMV RNA 4), Jobling et al. (1987) *Nature* 325:622-625); tobacco mosaic virus leader (TMV), Gallie et al. (1989) *Molecular Biology of RNA*, pages 237-256; and maize chlorotic mottle virus leader (MCMV) Lommel et al. (1991) *Virology* 81:382-385. See also Della-Cioppa et al. (1987) *Plant Physiology* 84:965-968. The cassette can also contain sequences that enhance translation and/or mRNA stability such as introns.

In those instances where it is desirable to have the expressed product of the isolated nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to: the transit peptide for the acyl carrier protein, the small subunit of RUBISCO, plant EPSP synthase, and the like.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions such as transitions and transversions, can be involved.

As noted herein, the present invention provides vectors capable of expressing genes of interest under the control of the regulatory elements. In general, the vectors should be functional in plant cells. At times, it may be preferable to have vectors that are functional in *E. coli* (e.g., production of protein for raising antibodies, DNA sequence analysis, construction of inserts, obtaining quantities of nucleic acids).

Vectors and procedures for cloning and expression in *E. coli* are discussed in Sambrook et al. (supra).

The transformation vector comprising the regulatory sequences of the present invention operably linked to an isolated nucleotide sequence in an expression cassette, can also contain at least one additional nucleotide sequence for a gene to be cotransformed into the organism. Alternatively, the additional sequence(s) can be provided on another transformation vector.

Vectors that are functional in plants can be binary plasmids derived from *Agrobacterium*. Such vectors are capable of transforming plant cells. These vectors contain left and right border sequences that are required for integration into the host (plant) chromosome. At minimum, between these border sequences is the gene to be expressed under control of the regulatory elements of the present invention. In one embodiment, a selectable marker and a reporter gene are also included. For ease of obtaining sufficient quantities of vector, a bacterial origin that allows replication in *E. coli* can be used.

Reporter genes can be included in the transformation vectors. Examples of suitable reporter genes known in the art can be found in, for example: Jefferson et al. (1991) in *Plant Molecular Biology Manual*, ed. Gelvin et al. (Kluwer Academic Publishers), pp. 1-33; DeWet et al. (1987) *Mol. Cell. Biol.* 7:725-737; Goff et al. (1990) *EMBO J.* 9:2517-2522; Kain et al. (1995) *BioTechniques* 19:650-655; and Chiu et al. (1996) *Current Biology* 6:325-330.

Selectable marker genes for selection of transformed cells or tissues can be included in the transformation vectors. These can include genes that confer antibiotic resistance or resistance to herbicides. Examples of suitable selectable marker genes include, but are not limited to: genes encoding resistance to chloramphenicol, Herrera Estrella et al. (1983) *EMBO J.* 2:987-992; methotrexate, Herrera Estrella et al. (1983) *Nature* 303:209-213; Meijer et al. (1991) *Plant Mol. Biol.* 16:807-820; hygromycin, Waldron et al. (1985) *Plant Mol. Biol.* 5:103-108; Zhijian et al. (1995) *Plant Science* 108:219-227; streptomycin, Jones et al. (1987) *Mol. Gen. Genet.* 210:86-91; spectinomycin, Bretagne-Sagnard et al. (1996) *Transgenic Res.* 5:131-137; bleomycin, Hille et al. (1990) *Plant Mol. Biol.* 7:171-176; sulfonamide, Guerineau et al. (1990) *Plant Mol. Biol.* 15:127-136; bromoxynil, Stalker et al. (1988) *Science* 242:419-423; glyphosate, Shaw et al. (1986) *Science* 233:478-481; phosphinothricin, DeBlock et al. (1987) *EMBO J.* 6:2513-2518.

Other genes that could serve utility in the recovery of transgenic events but might not be required in the final product would include, but are not limited to: GUS (β-glucoronidase), Jefferson (1987) *Plant Mol. Biol. Rep.* 5:387); GFP (green florescence protein), Chalfie et al. (1994) *Science* 263: 802; luciferase, Teeri et al. (1989) *EMBO J.* 8:343; and the maize genes encoding for anthocyanin production, Ludwig et al. (1990) *Science* 247:449.

The transformation vector comprising the particular regulatory sequences of the present invention, operably linked to an isolated nucleotide sequence of interest in an expression cassette, can be used to transform any plant. In this manner, genetically modified plants, plant cells, plant tissue, seed, and the like can be obtained. Transformation protocols can vary depending on the type of plant or plant cell, i.e., monocot or dicot, targeted for transformation. Suitable methods of transforming plant cells include microinjection, Crossway et al. (1986) *Biotechniques* 4:320-334; electroporation, Riggs et al. (1986) *Proc. Natl. Acad. Sci.* USA 83:5602-5606; *Agrobacterium*-mediated transformation, see for example, Townsend et al. U.S. Pat. No. 5,563,055; direct gene transfer, Paszkowski et al. (1984) *EMBO J.* 3:2717-2722; and ballistic particle acceleration, see for example, Sanford et al. U.S. Pat. No. 4,945,050; Tomes et al. (1995) in *Plant Cell, Tissue, and Organ Culture: Fundamental Methods*, ed. Gamborg and Phillips (Springer-Verlag, Berlin); and McCabe et al. (1988) *Biotechnology* 6:923-926. Also see Weissinger et al. (1988) *Annual Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Datta et al. (1990) *Biotechnology* 8:736-740 (rice); Klein et al. (1988) *Proc. Natl. Acad. Sci.* USA 85:4305-4309 (maize); Klein et al. (1988) *Biotechnology* 6:559-563 (maize); Klein et al. (1988) *Plant Physiol.* 91:440-444 (maize); Fromm et al. (1990) *Biotechnology* 8:833-839; Hooydaas-Van Slogteren et al. (1984) *Nature* (London) 311:763-764; Bytebier et al. (1987) *Proc. Natl. Acad. Sci.* USA 84:5345-5349 (Liliaceae); De Wet et al. (1985) in *The Expenmental Manipulation of Ovule Tissues*, ed. G. P. Chapman et al. (Longman, New York), pp. 197-209 (pollen); Kaeppler et al. (1990) *Plant Cell Reports* 9:415-418; and Kaeppler et al. (1992) *Theor. Appl. Genet.* 84:560-566 (whisker-mediated transformation); D. Halluin et al. (1992) *Plant Cell* 4:1495-1505 (electroporation); Li et al. (1993) *Plant Cell Reports* 12:250-255 and Christou et al. (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The cells that have been transformed can be grown into plants in accordance with conventional ways. See, for example, McCormick et al. (1986) *Plant Cell Reports* 5:81-84. These plants can then be grown and pollinated with the same transformed strain or different strains. The resulting hybrid having seed-preferred expression of the desired phenotypic characteristic can then be identified. Two or more generations can be grown to ensure that seed-preferred expression of the desired phenotypic characteristic is stably maintained and inherited.

The following examples are offered by way of illustration and not by way of limitation.

EXAMPLES

The regulatory regions of the invention were isolated from maize plants and cloned. The genes were selected as a source for a seed-preferred regulatory regions based on the spatial expression of their gene products. The method for their isolation is described below.

Example 1

Isolation of Promoter Sequences Using Genome Walker

The procedure for promoter isolation is described in the User Manual for the Genome Walker kit sold by Clontech Laboratories, Inc., Palo Alto, Calif. Genomic DNA from maize line V3-4 A63 was prepared by grinding 10-day-old seedling leaves in liquid nitrogen, and the DNA prepared as described by Chen and Dellaporta (1994) in The Maize Handbook, ed. Freeling and Walbot (Springer-Verlag, Berlin) with a few minor modifications as follows: precipitated DNA was recovered using an inoculation loop and transferred to a 1.5 ml eppendorf tube containing 500 μl of TE (10 mM Tris pH 8.0, 1 mM EDTA). The DNA was allowed to dissolve at room temperature for 15 minutes, phenol extracted and 2-propanol precipitated in 700 μl. The precipitate was recovered and washed with 70% ethanol. The DNA was then placed in a clean 1.5 ml eppendorf tube to air dry and resuspended in 200 µl of TE. RNase A was added to 10 µg/ml and the mixture was incubated at 37° C. for several hours. The DNA was then extracted once with phenol-chloroform, then chloroform, then ethanol precipitated and resuspended in TE. The DNA was then used as described in the Genome Walker User Manual (Clontech PT3042-1 version PR68687) with the following modifications: briefly, the DNA was digested separately with restriction enzymes DraI, EcoRV, PvuII, ScaI, StuI, HpaI, EcoICRI, XmnI, and SspI all blunt-end cutters. The DNA was extracted with phenol, then chloroform, then ethanol precipitated. The Genome Walker adapters were ligated onto the ends of the restricted DNA. The resulting DNA is referred to as DL1-DL9, respectively.

For isolation of Jip1 and mi1ps3 promoter regions, two nonoverlapping gene-specific primers (26-30 bp in length) were designed from the 5' end of the maize genes identified from sequence databases. The primers were designed to amplify the region upstream of the coding sequence, i.e. the 5' untranslated region and promoter of the chosen gene. The first round of PCR was performed on each DNA sample (DL1-9) with Clontech primer AP1 and the gene-specific primers (gsp)1 with the sequences shown in SEQ ID NOS: 2 and 5.

PCR was performed in a Bio-Rad icycler (Hercules, Calif.) thermal cycler using reagents supplied with the Genome Walker kit. The following cycle parameters were used: 7 cycles of 94° C. for 2 seconds, then 70° C. for 3 minutes, followed by 36 cycles of 94° C. for 2 seconds and 67° C. for 3 minutes. Finally, the samples were held at 67° C. for 4 minutes and then at 4° C. until further analysis.

For the mi1ps3 promoter, bands from the primary PCR (DL-1, DL-7, DL-8, and DL-9) were used to isolate the promoter sequence.

For the Jip1 promoter, as described in the User Manual, the DNA from the first round of PCR was then diluted and used as a template in a second round of PCR using the Clontech AP2 primer and gene-specific primers (gsp2) with the sequence shown in SEQ ID NO: 3.

The cycle parameters for the second round were: 5 cycles of 94° C. for 2 seconds, then 70° C. for 3 minutes, followed by 25 cycles of 94° C. for 2 seconds and 67° C. for 3 minutes. Finally, the samples were held at 67° C. for 4 minutes and then held at 4° C. Approximately 10 µl of each reaction were run on a 0.8% agarose gel, and bands (usually 500 bp or larger) were excised, purified with the Qiagen Gel Extraction Kit (Santa Clarita, Calif.) and cloned into the pGEM-T Easy vector (Promega Corp. Madison, Wis.). Clones were sequenced for verification.

After verification, the promoters were reisolated by amplifying new fragments from genomic DNA from maize line V3-4 A63 using primers created from the new promoter sequence. This was done to insure that sequences were error free. The PCR reaction was performed in a Bio-Rad icycler (Hercules, Calif.) thermal cycler using Hifidelity supermix (Cat.#10790-020, Life Technologies, Rockville Md.). The following cycle parameters were used: 94° C. for 2 seconds, followed by 30 cycles of 94° C. for 20 seconds, (55° C. for Jip1, 61° C. for mi1ps3) for 30 seconds, and 68° C. for 1 minute. Finally, the samples were held at 67° C. for 4 minutes and then at 4° C. until further analysis. The primers also contained sequences that would generate an NcoI site at the start codon. This was performed in order to create a translational fusion. For Jip1, these primers are shown in SEQ ID NOS: 13 and 14, for mi1ps3, they are shown in SEQ ID NOS: 15 and 16.

Example 2

Isolation of Promoter Sequences Using BAC (Bacterial Artificial Chromosome) Libraries The BAC library subjected to the screening procedure was produced from the maize Mo17 genotype using the protocol of Gubler and Hoffman (Gubler, U. et al. Gene, 1983; 25:263-269). Half of the library was digested with HindIII and half with EcoRI. The half cut with HindIII and screened for the Lec1 promoter consisted of approximately 69,000 clones. These clones were plated out on 22×22 cm2 agar plate at density of about 3,000 colonies per plate. The plates were incubated in a 37° C. incubator for 12-24 hours. Colonies were picked into 384-well plates by a robot colony picker, Q-bot (GENETIX Limited). These plates were incubated overnight at 37° C.

Once sufficient colonies were picked, they were pinned onto 22×22 cm2 nylon membranes using Q-bot. Each membrane contained 9,216 colonies or 36,864 colonies. These membranes were placed onto agar plate with appropriate antibiotic. The plates were incubated at 37° C. for overnight. After colonies were recovered on the second day, these filters were placed on filter paper prewetted with denaturing solution for four minutes, then were incubated on top of a boiling water bath for additional four minutes. The filters were then placed on filter paper prewetted with neutralizing solution for four minutes. After excess solution was removed by placing the filters on dry filter papers for one minute, the colony side of the filters were place into Proteinase K solution, incubated at 37° C. for 40-50 minutes. The filters were placed on dry filter papers to dry overnight. DNA was then cross-linked to nylon membrane by UV light treatment.

Colony hybridization was conducted as described by Sambrook, J., Fritsch, E. F. and Maniatis, T., (in Molecular Cloning: A laboratory Manual, 2nd Edition). The probe was used in colony hybridization. The probe was created in a PCR reaction using the Advantage GC genomic PCR Kit (Clontech, Palo alto, Calif.) with 5% GC melt. Genomic DNA from maize line V3-4 A63 was amplified with a forward and reverse primer: SEQ ID NOS: 8, and 9. The PCR reaction was performed in a Bio-Rad icycler (Hercules, Calif.) thermal cycler using Hifidelity supermix (Cat.#10790-020, Life Technologies, Rockville Md.). The following cycle parameters were used: 94° C. for 2 seconds, followed by 30 cycles of 94° C. for 20 seconds, 63° C. for 30 seconds, and 68° C. for 1 minute. Finally, the samples were held at 67° C. for 4 minutes and then at 4° C. until further analysis.

Once positive BACs were identified, a southern analysis using a HindIII digestion was performed on them to identify bands containing Lec1 for subcloning. The same probe was used to identify a fragment (~4 kb) which was positive for Lec1. This band was subcloned into the pBS2KS+ cloning vector (Stratagene Inc., 11011 N. Torrey Pines Rd., La Jolla, Calif.; www.strategene.com) and sequenced. The band contained 1.4 kb of sequence upstream of the coding region of Lec1 and 1.7 kb of sequence downstream. The Lec1 promoter and terminator regions were obtained using primers SEQ ID NOS: 17, 18, 19 and 20, created from this sequence to amplify genomic DNA from maize line A63. The PCR reaction was performed in a Bio-Rad icycler (Hercules, Calif.) thermal cycler using Hifidelity supermix (Cat.#10790-020, Life Technologies, Rockville Md.). The following cycle parameters were used: 94° C. for 2 seconds, followed by 30 cycles of 94° C. for 20 seconds, 58° C. for 30 seconds, and 68° C. for 1 minute. Finally, the samples were held at 67° C. for 4 minutes and then at 4° C. until further analysis. The PCR products were then cloned into the pGEM-T Easy vector (Promega Corp. Madison, Wis.). Clones were sequenced for verification.

Example 3

Expression Data Using Promoter Sequences

Promoter: GUS fusion constructs were prepared by the methods described below. All vectors were constructed using standard molecular biology techniques (Sambrook et al., Supra). A reporter gene and a selectable marker gene for gene expression and selection was inserted between the multiple cloning sites of the pBluescript cloning vector (Stratagene Inc., 11011 N. Torrey Pines Rd., La Jolla, Calif.; www.strategene.com). The ampicillin resistence gene was replaced with a kanamycin resistance gene to allow use in bombardment experiments. The reporter gene was the β-glucuronidase (GUS) gene (Jefferson, R. A. et al., 1986, Proc. Natl. Acad. Sci. (USA) 83:8447-8451) into whose coding region was inserted the second intron from the potato ST-LS1 gene (Vancanneyt et al., Mol. Gen. Genet. 220:245-250, 1990), to produce GUSINT, in order to prevent expression of the gene in *Agrobacterium* (see Ohta, S. et al., 1990, Plant Cell Physiol. 31(6):805-813. A fragment containing bases 2 to 310 from the terminator of the potato proteinase inhibitor (pinII) gene (An et al., Plant Cell 1:115-122, 1989) was blunt-end ligated downstream of the GUS coding sequence, to create the GUS expression cassette. The 3' end of the terminator carried a NotI restriction site. The respective promoter regions were ligated in frame to the NcoI site 5' to the GUS gene at the start codon.

Jip1::GUS::pinII was constructed using the above plasmid digested with NcoI, and PstI to provide insertion sites for the promoter. The plasmid with the isolated Jip1 promoter in the pGEM-T Easy cloning vector was digested with NcoI, and PstI. The fragment was ligated into the digested expression cassette and successful subcloning was confirmed by restriction analysis.

mi1ps3::GUS::pinII was constructed using the GUSINT:: pinII cassette. The cassette was digested with NcoI and HindIII. The mi1ps3 promoter contained in the pGEM-T Easy cloning vector was isolated through digestion with NcoI and HindIII. The fragment was ligated into the digested expression cassette and successful subcloning was confirmed by restriction analysis.

Lec1::GUS::Lec1 was prepared using the GUS::pinII cassette digested digested with NcoI/HindIII, which had been modified to have a BglIII site at the 3' end of the GUSINT coding region. The Lec1 promoter in pGEM-T Easy was digested with NcoI and HindIII. The fragment was then ligated into the vector and confirmed by restriction analysis and sequencing. The Lec1 terminator was digested with BglII/EcoRI and ligated into the Lec1::GUS::PINII plasmid digested with BglII/EcoRI. Successful subcloning was confirmed by restriction analysis.

The *Agrobacterium* transformation plasmids were constructed by inserting the GUS expression cassettes as BstEII fragments into a descendent plasmid of pSB11 which contained the BAR expression cassette. Both the GUS, and BAR expression cassettes were located between the right and left T-DNA. The GUS cassette was inserted proximal to the right T-DNA border. The plasmid pSB11 was obtained from Japan Tobacco Inc. (Tokyo, Japan). The construction of pSB11 from pSB21 and the construction of pSB21 from starting vectors is described by Komari et al. (1996, Plant J. 10:165-174). The T-DNA of the plasmid was integrated into the superbinary plasmid pSB1 (Saito et al., EP 672 752 A1) by homologous recombination between the two plasmids. The plasmid pSB1 was also obtained from Japan Tobacco Inc.

Competent cells of the *Agrobacterium* strain LBA4404 harboring pSB1 were created using the protocol as described by Lin (1995) in Methods in Molecular Biology, ed. Nickoloff, J. A. (Humana Press, Totowa, N.J.) The plasmid containing the expression cassettes was electroporated into competent cells of the *Agrobacterium* strain LBA4404 harboring pSB1 to create the cointegrate plasmid in *Agrobacterium* using a BIO-RAD Micropulser (Cat#165-2100, Hercules, Calif.). Electroporation was performed by mixing 1 ul of plasmid DNA (~100 ng) with 20 μl of competent *Agrobacterium* cells in a 0.2 cm electrode gap cuvette (Cat#165-2086, BIO-RAD, Hercules, Calif.). Electroporation was performed using the EC2 setting, which delivers 2.5 kV to the cells. Successful recombination was verified by restriction analysis of the plasmid after transformation of the cointegrate plasmid back into *E. coli* DH5a cells.

Example 4

Transformation and Regeneration of Maize Callus Via *Agrobacterium*

Preparation of *Agrobacterium* Suspension:

*Agrobacterium* was streaked out from a −80° frozen aliquot onto a plate containing PHI-L medium and cultured at 28° C. in the dark for 3 days. PHI-L media comprises 25 ml/l Stock Solution A, 25 ml/l Stock Solution B, 450.9 ml/l Stock Solution C and spectinomycin (Sigma Chemicals) added to a concentration of 50 mg/l in sterile ddH2O (stock solution A: K2HPO4 60.0 g/l, NaH2PO4 20.0 g/l, adjust pH to 7.0 w/KOH and autoclaved; stock solution B: NH4Cl 20.0 g/l, MgSO4.7H2O 6.0 g/l, KCl 3.0 g/l, CaCl2 0.20 g/l, FeSO4.7H2O 50.0 mg/l, autoclaved; stock solution C: glucose 5.56 g/l, agar 16.67 g/l (#A-7049, Sigma Chemicals, St. Louis, Mo.) and autoclaved).

The plate can be stored at 4° C. and used usually for about 1 month. A single colony was picked from the master plate and streaked onto a plate containing PHI-M medium [yeast extract (Difco) 5.0 g/l; peptone (Difco) 10.0 g/l; NaCl 5.0 g/l; agar (Difco) 15.0 g/l; pH 6.8, containing 50 mg/L spectinomycin] and incubated at 28° C. in the dark for 2 days.

Five ml of either PHI-A, [CHU(N6) basal salts (Sigma C-1416) 4.0 g/l, Eriksson's vitamin mix (1000×, Sigma-1511) 1.0 ml/l; thiamine.HCl 0.5 mg/l (Sigma); 2,4-dichlorophenoxyacetic acid (2,4-D, Sigma) 1.5 mg/l; L-proline (Sigma) 0.69 g/l; sucrose (Mallinckrodt) 68.5 g/l; glucose (Mallinckrodt) 36.0 g/l; pH 5.2] for the PHI basic medium system, or PHI-I [MS salts (GIBCO BRL) 4.3 g/l; nicotinic acid (Sigma) 0.5 mg/l; pyridoxine.HCl (Sigma) 0.5 mg/l; thiamine.HCl 1.0 mg/l; myo-inositol (Sigma) 0.10 g/l; vitamin assay casamino acids (Difco Lab) 1 g/l; 2,4-D 1.5 mg/l; sucrose 68.50 g/l; glucose 36.0 g/l; adjust pH to 5.2 w/KOH and filter-sterilize] for the PHI combined medium system and 5 ml of 100 mM (3'-5'-Dimethoxy4'-hydroxyacetophenone, Aldrich chemicals) were added to a 14 ml Falcon tube in a hood. About 3 full loops (5 mm loop size) *Agrobacterium* was collected from the plate and suspended in the tube, then the tube vortexed to make an even suspension. One ml of the suspension was transferred to a spectrophotometer tube and the OD of the suspension adjusted to 0.72 at 550 nm by adding either more *Agrobacterium* or more of the same suspension medium, for an *Agrobacterium* concentration of approximately 0.5×109 cfu/ml to 1×109 cfu/ml. The final *Agrobac*-

*terium* suspension was aliquoted into 2 ml microcentrifuge tubes, each containing 1 ml of the suspension. The suspensions were then used as soon as possible.

Embryo Isolation, Infection and Co-Cultivation:

About 2 ml of the same medium (here PHI-A or PHI-I) used for the *Agrobacterium* suspension were added into a 2 ml microcentrifuge tube. Immature embryos were isolated from a sterilized ear with a sterile spatula (Baxter Scientific Products S1565) and dropped directly into the medium in the tube. A total of about 100 embryos were placed in the tube. The optimal size of the embryos was about 1.0-1.2 mm. The cap was then closed on the tube and the tube vortexed with a Vortex Mixer (Baxter Scientific Products S8223-1) for 5 sec. at maximum speed. The medium was removed and 2 ml of fresh medium were added and the vortexing repeated. All of the medium was drawn off and 1 ml of *Agrobacterium* suspension added to the embryos and the tube vortexed for 30 sec. The tube was allowed to stand for 5 min. in the hood. The suspension of *Agrobacterium* and embryos was poured into a Petri plate containing either PHI-B medium [CHU(N6) basal salts (Sigma C-1416) 4.0 g/l; Eriksson's vitamin mix (1000×, Sigma-1511) 1.0 ml/l; thiamine.HCl 0.5 mg/l; 2,4-D 1.5 mg/l; L-proline 0.69 g/l; silver nitrate 0.85 mg/l; gelrite (Sigma) 3.0 g/l; sucrose 30.0 g/l; acetosyringone 100 mM; pH 5.8], for the PHI basic medium system, or PHI-J medium [MS Salts 4.3 g/l; nicotinic acid 0.50 mg/l; pyridoxine HCl 0.50 mg/l; thiamine.HCl 1.0 mg/l; myo-inositol 100.0 mg/l; 2,4-D 1.5 mg/l; sucrose 20.0 g/l; glucose 10.0 g/l; L-proline 0.70 g/l; MES (Sigma) 0.50 g/l; 8.0 g/l agar (Sigma A-7049, purified) and 100 mM acetosyringone with a final pH of 5.8 for the PHI combined medium system. Any embryos left in the tube were transferred to the plate using a sterile spatula. The *Agrobacterium* suspension was drawn off and the embryos placed axis side down on the media. The plate was sealed with Parafilm tape or Pylon Vegetative Combine Tape (product named "E.G.CUT" and is available in 18 mm×50 m sections; Kyowa Ltd., Japan) and incubated in the dark at 23-25° C. for about 3 days of co-cultivation.

Resting, Selection and Regeneration Steps:

For the resting step, all of the embryos were transferred to a new plate containing PHI-C medium [CHU(N6) basal salts (Sigma C-1416) 4.0 g/l; Eriksson's vitamin mix (1000× Sigma-1511) 1.0 ml/l; thiamine.HCl 0.5 mg/l; 2,4-D 1.5 mg/l; L-proline 0.69 g/l; sucrose 30.0 g/l; MES buffer (Sigma) 0.5 g/l; agar (Sigma A-7049, purified) 8.0 g/l; silver nitrate 0.85 mg/l; carbenicillin 100 mg/l; pH 5.8]. The plate was sealed with Parafilm or Pylon tape and incubated in the dark at 28° C. for 3-5 days.

Longer co-cultivation periods may compensate for the absence of a resting step since the resting step, like the co-cultivation step, provides a period of time for the embryo to be cultured in the absence of a selective agent. Those of ordinary skill in the art can readily test combinations of co-cultivation and resting times to optimize or improve the transformation For selection, all of the embryos were then transferred from the PHI-C medium to new plates containing PHI-D medium, as a selection medium, [CHU(N6) basal salts (SIGMA C-1416) 4.0 g/l; Eriksson's vitamin mix (1000×, Sigma-1511) 1.0 ml/l; thiamine.HCl 0.5 mg/l; 2,4-D 1.5 mg/l; L-proline 0.69 g/l; sucrose 30.0 g/l; MES buffer 0.5 g/l; agar (Sigma A-7049, purified) 8.0 g/l; silver nitrate 0.85 mg/l; carbenicillin (ICN, Costa Mesa, Calif.) 100 mg/l; bialaphos (Meiji Seika K.K., Tokyo, Japan) 1.5 mg/l for the first two weeks followed by 3 mg/l for the remainder of the time.; pH 5.8] putting about 20 embryos onto each plate.

The plates were sealed as described above and incubated in the dark at 28° C. for the first two weeks of selection. The embryos were transferred to fresh selection medium at two-week intervals. The tissue was subcultured by transferring to fresh selection medium for a total of about 2 months. The herbicide-resistant calli were then "bulked up" by growing on the same medium for another two weeks until the diameter of the calli was about 1.5-2 cm.

For regeneration, the calli were then cultured on PHI-E medium [MS salts 4.3 g/l; myo-inositol 0.1 g/l; nicotinic acid 0.5 mg/l, thiamine.HCl 0.1 mg/l, Pyridoxine.HCl 0.5 mg/l, Glycine 2.0 mg/l, Zeatin 0.5 mg/l, sucrose 60.0 g/l, Agar (Sigma, A-7049) 8.0 g/l, Indoleacetic acid (IAA, Sigma) 1.0 mg/l, Abscisic acid (ABA, Sigma) 0.1 mM, Bialaphos 3 mg/l, carbenicillin 100 mg/l adjusted to pH 5.6] in the dark at 28° C. for 1-3 weeks to allow somatic embryos to mature. The calli were then cultured on PHI-F medium (MS salts 4.3 g/l; myo-inositol 0.1 g/l; Thiamine.HCl 0.1 mg/l, Pyridoxine.HCl 0.5 mg/l, Glycine 2.0 mg/l, nicotinic acid 0.5 mg/l; sucrose 40.0 g/l; gelrite 1.5 g/l; pH 5.6] at 25° C. under a daylight schedule of 16 hrs. light (270 uE m-2sec-1) and 8 hrs. dark until shoots and roots developed. Each small plantlet was then transferred to a 25×150 mm tube containing PHI-F medium and grown under the same conditions for approximately another week. The plants were transplanted to pots with soil mixture in a greenhouse. GUS+ events are determined at the callus stage or regenerated plant stage.

For Hi-II, an optimized protocol was: 0.5×10⁹ cfu/ml *Agrobacterium*, a 3-5 day resting step, and no AgNO3 in the infection medium (PHI-A medium).

Example 5

Transformation of Maize by Particle Bombardment

The inventive polynucleotides contained within a vector were transformed into embryogenic maize callus by particle bombardment. Transgenic maize plants were produced by bombardment of embryogenically responsive immature embryos with tungsten particles associated with DNA plasmid. The plasmid consisted of a selectable and an unselectable marker gene.

Preparation of Particles

Fifteen mg of tungsten particles (General Electric), 0.5 to 1.8 µ, preferably 1 to 1.8 µ, and most preferably 1 µ, were added to 2 ml of concentrated nitric acid. This suspension was sonicated at 0° C. for 20 minutes (Branson Sonifier Model 450, 40% output, constant duty cycle). Tungsten particles were pelleted by centrifugation at 10000 rpm (Biofuge) for one minute, and the supernatant removed. Two milliliters of sterile distilled water were added to the pellet, and brief sonication used to resuspend the particles. The suspension was pelleted, one milliliter of absolute ethanol added to the pellet, and brief sonication used to resuspend the particles. Rinsing, pelleting, and resuspending of the particles was performed two more times with sterile distilled water, and finally the particles resuspended in two milliliters of sterile distilled water. The particles were subdivided into 250-ml aliquots and stored frozen.

Preparation of Particle-Plasmid DNA Association

The stock of tungsten particles was sonicated briefly in a water bath sonicator (Branson Sonifier Model 450, 20% output, constant duty cycle) and 50 ml transferred to a microfuge tube. Equimolar amounts of plasmid DNA are added to the particles for a final DNA amount of 0.1 to 10 mg in 10 ml total volume, and briefly sonicated: 1 mg total DNA was used.

Fifty microliters of sterile aqueous 2.5 M CaCl2 were added, and the mixture briefly sonicated and vortexed. Twenty microliters of sterile aqueous 0.1 M spermidine were added and the mixture briefly sonicated and vortexed. The mixture was incubated at room temperature for 20 minutes with intermittent brief sonication. The particle suspension was centrifuged, and the supernatant removed. Two hundred fifty microliters of absolute ethanol were added to the pellet, followed by brief sonication. The suspension was pelleted, the supernatant removed, and 60 ml of absolute ethanol added. The suspension was sonicated briefly before loading the particle-DNA agglomeration onto macrocarriers.

Preparation of Tissue

Immature embryos of maize variety High Type II were the target for particle bombardment-mediated transformation. This genotype is the F1 of two purebred genetic lines, parents A and B, derived from the cross of two know maize inbreds, A188 and B73. Both parents were selected for high competence of somatic embryogenesis, according to Armstrong et al., Maize Genetics Coop. News 65:92 (1991).

Ears from F1 plants were selfed or sibbed, and embryos aseptically dissected from developing caryopses when the scutellum first became opaque. This stage occurs about 9-13 days post-pollination, and most generally about 10 days post-pollination, depending on growth conditions. The embryos were about 0.75 to 1.5 millimeters long. Ears were surface sterilized with 20-50% Clorox for 30 minutes, followed by three rinses with sterile distilled water.

Immature embryos were cultured with the scutellum oriented upward, on embryogenic induction medium comprised of N6 basal salts, Eriksson vitamins, 0.5 mg/l thiamine HCl, 30 gm/l sucrose, 2.88 gm/l L-proline, 1 mg/l 2,4-dichlorophenoxyacetic acid, 2 gm/l Gelrite, and 8.5 mg/l AgNO3. Chu et al., Sci. Sin. 18:659 (1975); Eriksson, Physiol. Plant 18:976 (1965).

The medium was sterilized by autoclaving at 121° C. for 15 minutes and dispensed into 100×25 mm Petri dishes. AgNO3 was filter-sterilized and added to the medium after autoclaving. The tissues were cultured in complete darkness at 28° C. After about 3 to 7 days, most usually about 4 days, the scutellum of the embryo swelled to about double its original size and the protuberances at the coleorhizal surface of the scutellum indicated the inception of embryogenic tissue. Up to 100% of the embryos displayed this response, but most commonly, the embryogenic response frequency was about 80%.

When the embryogenic response was observed, the embryos were transferred to a medium comprised of induction medium modified to contain 120 gm/l sucrose. The embryos were oriented with the coleorhizal pole—the embryogenically responsive tissue—upwards from the culture medium. Ten embryos per Petri dish were located in the center of a Petri dish in an area about 2 cm in diameter. The embryos were maintained on this medium for 3-16 hour, preferably 4 hours, in complete darkness at 28° C. just prior to bombardment with particles associated with plasmid DNA containing the selectable and unselectable marker genes.

To effect particle bombardment of embryos, the particle-DNA agglomerates were accelerated using a DuPont PDS-1000 particle acceleration device. The particle-DNA agglomeration was briefly sonicated and 10 ml were deposited on macrocarriers and the ethanol allowed to evaporate. The macrocarrier was accelerated onto a stainless-steel stopping screen by the rupture of a polymer diaphragm (rupture disk). Rupture is effected by pressurized helium. The velocity of particle-DNA acceleration is determined based on the rupture disk breaking pressure. Rupture disk pressures of 200 to 1800 psi were used. Multiple disks were used to effect a range of rupture pressures.

The shelf containing the plate with embryos was placed 5.1 cm below the bottom of the macrocarrier platform (shelf #3). To effect particle bombardment of cultured immature embryos, a rupture disk and a macrocarrier with dried particle-DNA agglomerates were installed in the device. The He pressure delivered to the device was adjusted to 200 psi above the rupture disk breaking pressure. A Petri dish with the target embryos was placed into the vacuum chamber and located in the projected path of accelerated particles. A vacuum was created in the chamber, preferably about 28 in Hg. After operation of the device, the vacuum was released and the Petri dish removed.

Bombarded embryos remain on the osmotically-adjusted medium during bombardment, and 1 to 4 days subsequently. The embryos are transferred to selection medium comprised of N6 basal salts, Eriksson vitamins, 0.5 mg/1 thiamine HCl, 30 gm/l sucrose, 1 mg/l 2,4-dichlorophenoxyacetic acid, 2 gm/l Gelrite, 0.85 mg/l Ag NO3 and 3 mg/l bialaphos (Herbiace, Meiji). Bialaphos was added filter-sterilized. The embryos were subcultured to fresh selection medium at 10 to 14 day intervals. After about 7 weeks, embryogenic tissue, putatively transformed for both selectable and unselected marker genes, proliferated from the bombarded embryos. Putative transgenic tissue was rescued, and that tissue derived from individual embryos was considered to be an event and propagated independently on selection medium. Two cycles of clonal propagation were achieved by visual selection for the smallest contiguous fragments of organized embryogenic tissue.

For regeneration of transgenic plants, embryogenic tissue was subcultured to a medium comprising MS salts and vitamins (Murashige & Skoog, Physiol. Plant 15: 473 (1962)), 100 mg/l myo-inositol, 60 gm/l sucrose, 3 gm/l Gelrite, 0.5 mg/l zeatin, 1 mg/l indole-3-acetic acid, 26.4 ng/l cis-trans-abscissic acid, and 3 mg/l bialaphos in 100×25 mm Petri dishes, and incubated in darkness at 28° C. until the development of well-formed, matured somatic embryos could be seen. This required about 14 days. Well-formed somatic embryos were opaque and cream-colored, and comprised of an identifiable scutellum and coleoptile. The embryos were individually subcultured to a germination medium comprising MS salts and vitamins, 100 mg/l myo-inositol, 40 gm/l sucrose and 1.5 gm/l Gelrite in 100×25 mm Petri dishes and incubated under a 16 hour light::8 hour dark photoperiod and 40 meinsteinsm-2sec-1 from cool-white fluorescent tubes. After about 7 days, the somatic embryos germinated and produced a well-defined shoot and root. The individual plants were subcultured to germination medium in 125×25 mm glass tubes to allow further plant development. The plants were maintained under a 16 hour light:8 hour dark photoperiod and 40 meinsteinsm-2sec-1 from cool-white fluorescent tubes. After about 7 days, the plants were well-established and transplanted to horticultural soil, hardened off, and potted into commercial greenhouse soil mixture and grown to sexual maturity in a greenhouse.

Example 6

Northern Analysis of Gene Expression in Vegetative Tissue and Developing Kernels Total RNA (10 µg) was size fractionated on a 1% formaldehyde agarose gel and transferred to a nitrocellulose membrane. In separate experiments, membranes were hybridized under stringent conditions with 32P-labelled probes representing cDNA fragments of Jip1 and Lec1. After extensive washing to remove unbound probe, membranes were exposed on X-ray film. RNA samples were obtained from vegetative tissues (Tassel, leaf, primary root) as well as developing maize kernels.

The Jip1 expression pattern showed no expression in vegetative tissues or 0-5 DAP whole kernel. Jip1 was predominantly expressed in 15-40 DAP embryo with some weaker expression in the endosperm and pericarp.

The Lec1 expression pattern showed no expression in vegetative tissues or endosperm tissues. Lec1 was predominately expressed in 10 DAP embryo tissue with weaker expression in 15 DAP embryo. Expression was off by 20 DAP in the embryo.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications can be practiced within the scope of the appended claims.

What is claimed is:

1. An isolated promoter that drives transcription in a plant or plant callus tissue, wherein the promoter comprises the nucleotide sequence set forth in SEQ ID NO: 6.

2. An expression cassette comprising a promoter operably linked to a nucleotide sequence wherein the promoter comprises the nucleotide sequence of claim 1.

3. A plant stably transformed with an expression cassette of claim 2.

4. The plant of claim 3, wherein said plant is a monocot.

5. The plant of claim 3, wherein said monocot is maize, wheat, rice, barley, sorghum, or rye.

6. Seed of the plant of claim 3, wherein the seed comprises the expression cassette.

7. A method for selectively expressing a nucleotide sequence in a plant cell, the method comprising:
   a) transforming a plant cell with an expression cassette, the expression cassette comprising a promoter operably linked to a nucleotide sequence wherein the promoter comprises
      the nucleotide sequence set forth in SEQ ID NO: 6; and
   b) growing the plant cell to selectively express the nucleotide sequence.

8. The method of claim 7 wherein the promoter initiates transient expression of the nucleotide sequence in callus tissue.

9. The method of claim 7 further comprising regenerating a stably transformed plant from the plant cell; wherein expression of the nucleotide sequence alters the phenotype of a plant.

10. The plant of claim 9, wherein said plant is a monocot.

11. The plant of claim 9, wherein said monocot is maize, wheat, rice, barley, sorghum, or rye.

12. Seed of the plant of claim 9, wherein the seed comprises the expression cassette.

* * * * *